United States Patent
Wetterich et al.

(10) Patent No.: US 6,410,486 B2
(45) Date of Patent: Jun. 25, 2002

(54) CYCLOALKYLALKANECARBOXAMIDES AND THEIR PREPARATION AND USE

(75) Inventors: Frank Wetterich, Mutterstadt; Karl Eicken, Wachenheim; Gisela Lorenz, Neustadt; Eberhard Ammermann, Heppenheim; Siegfried Strathmann, Limburgerhof; Ingo Rose, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/867,524

(22) Filed: May 31, 2001

Related U.S. Application Data

(62) Division of application No. 09/381,050, filed as application No. PCT/EP98/01031 on Feb. 23, 1998, now Pat. No. 6,265,447.

(30) Foreign Application Priority Data

Mar. 14, 1997 (DE) .......................................... 197 10 618

(51) Int. Cl.⁷ ........................ A01N 37/34; C07C 255/00
(52) U.S. Cl. ........................................ 504/312; 558/445
(58) Field of Search ........................... 504/312; 558/445

(56) References Cited

U.S. PATENT DOCUMENTS 4,946,867 A * 8/1990 Manabe et al. ............. 514/521

OTHER PUBLICATIONS

Liese et al., *Synthesis*, pp. 25–32, Jan. 1988.

\* cited by examiner

*Primary Examiner*—T A Solola
*Assistant Examiner*—Joseph Murray
(74) *Attorney, Agent, or Firm*—Keil & Weinkauf

(57) ABSTRACT

The present invention relates to novel cycloalkylalkane-carboxamides of the formula I

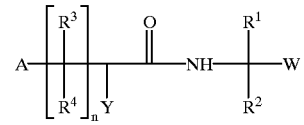

where the substituents have the following meanings:

A is $C_3$–$C_6$-cycloalkyl;

$R^1$ is $C_1$–$C_6$-alkyl or $C_2$–$C_6$-alkenyl;

$R^2$, $R^3$ and $R^4$ are hydrogen or, independently of this meaning, have one of the meanings of the radical $R^1$;

n is 0 or 1;

Y is cyano or halogen;

w is phenyl, naphthyl or heteroaryl.

17 Claims, No Drawings

CYCLOALKYLALKANECARBOXAMIDES AND THEIR PREPARATION AND USE

This application is a Divisional of Ser. No. 09/381,050 filed Sep. 14, 1999, which U.S. Pat. No. 6,265,447 is a 371 of PCT EP98/01031 filed Feb. 23, 1998.

The present invention relates to novel cycloalkylalkanecarboxamides of the formula I

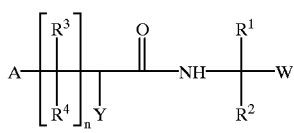

where the substituents have the following meanings:
A is $C_3$–$C_6$-cycloalkyl which can have attached to it one to three substituents selected from the group consisting of halogen and $C_1$–$C_3$-alkyl;
$R^1$ is $C_1$–$C_6$-alkyl or $C_2$–$C_6$-alkenyl, it being possible for these radicals to be partially or fully halogenated and/or to have attached to them one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl and phenyl, it being possible for the phenyl to be partially or fully halogenated and/or have attached to it one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl or heterocyclyl;
$R^2$, $R^3$, $R^4$ are hydrogen or, independently of this meaning, have one of the meanings of the radical $R^1$;
n is 0 or 1;
Y is cyano or halogen;
W is phenyl, naphthyl or heteroaryl, it being possible for these radicals to have attached to them one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl and $C_1$–$C_4$-alkoxycarbonyl,
with the exception of the compounds of the formula I where
n is 0 and
A is cyclopentyl.

α-Halo- and α-cyano-substituted carboxamides have already been disclosed in the literature for controlling harmful fungi, in particular for controlling Pyricularia oryzae (JP-A 57 185202, JP-A 57 188552, JP-A 57 188551, JP-A 58 029751, JP-A 58 029752, WO 95/31432, JP-A 07 206608, JP-A 07 330511, JP-A 08 012508 and U.S. Pat. No. 4,946, 867). J. Pestic. Sci. 12 (1987), 79–84, compiles work relating to the α-halo-substituted carboxamides published to date. This publication also attempts to establish quantitative relationships between structure and effect for this class of fungicides.

U.S. Pat. No. 4,946,867 mentions a cyanoacetamide derivative with a cyclopentyl group in the α-position, N-[1-(4-chlorophenyl)ethyl]-2-cyano-2-cyclopentylethanamide.

Since the fungicidal properties of the known compounds are not always fully satisfactory regarding their activity against harmful fungi, eg. Pyricularia oryzae, it is an object of the present invention to find novel carboxamides which are more active against harmful fungi, eg. Pyricularia oryzae.

We have found that this object is achieved by the novel cycloalkylalkanecarboxamides I defined at the outset.

Moreover, we have found processes for the preparation of the compounds I and the intermediates of the formula II required for their preparation. We have found compositions which comprise the compounds I, methods of controlling harmful fungi using the compounds I and finally, the use of the compounds I for controlling harmful fungi.

Depending on the substitution pattern, the compounds of the formula I may contain one or more chiral centers. In this case, they exist as enantiomer and diastereomer mixtures. The invention relates to the pure enantiomers and diastereomers and also to mixtures of these.

In the definition of the compounds I given at the outset, collective terms which represent individual enumerations of each of the group members were used for the radicals $R^1$ to $R^4$, A and Z. The radicals alkyl, alkylthio, alkoxy, alkoxycarbonyl and alkenyl can be straight-chain or branched.

The radical cycloalkyl represents the unsubstituted skeleton if no specific substitution of a hydrogen by halogen or $C_1$–$C_3$-alkyl is mentioned. The radical definition cyclopentyl, for example, corresponds to the empirical formula $C_5H_{10}$.

The term "partially or fully halogenated" is intended to express that in groups characterized thus some or all of the hydrogen atoms may be replaced by identical or different halogen atoms. The meaning halogen represents in each case fluorine, chlorine, bromine or iodine.

Examples of other meanings are:

$C_1$–$C_4$-alkyl and the alkyl moieties of $C_1$–$C_4$-alkylthio: methyl, ethyl, propyl, 1-methylethyl, butyl, 1-methylpropyl, 2-methylpropyl and 1,1-dimethylethyl;

$C_1$–$C_6$-alkyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy and the alkoxy moieties of $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_2$–$C_6$-alkenyl: ethylene, prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methyl-prop-2-en-1-yl, 1-ethyl-2-methyl-prop-1-en-1-yl and 1-ethyl-2-methyl-prop-2-en-1-yl;

$C_3$–$C_6$-cycloalkyl: cyclopropyl, cyclobutyl, cyclopentyl, cyclohexyl;

heteroaryl: aromatic mono- or polycyclic radicals which, besides carbon ring members, can additionally contain 1 to 4 nitrogen atoms or 1 to 3 nitrogen atoms and one oxygen or one sulfur atom or one oxygen or one sulfur atom, eg.:

5-membered heteroaryl containing 1 to 3 nitrogen atoms: 5-membered heteroaryl ring groups which, in addition to carbon atoms, may contain 1 to 3 nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl containing 1 to 4 nitrogen atoms or 1 to 3 nitrogen atoms and 1 sulfur atom or oxygen atom or 1 oxygen or 1 sulfur atom: 5-membered heteroaryl ring groups which, in addition to carbon atoms, may contain 1 to 4 nitrogen atoms or 1 to 3 nitrogen atoms and 1 sulfur or oxygen atom or 1 oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl containing 1 to 3 nitrogen atoms or 1 nitrogen atom and/or one oxygen or sulfur atom: 5-membered heteroaryl ring groups which, in addition to carbon atoms, may contain 1 to 4 nitrogen atoms or 1 to 3 nitrogen atoms and 1 sulfur or oxygen atom or 1 oxygen or one sulfur atom as ring members and in which 2 adjacent carbon ring members or 1 nitrogen and 1 adjacent carbon ring member may be bridged by a buta-1,3-diene-1,4-diyl group;

5-membered heteroaryl bonded via nitrogen and containing 1 to 4 nitrogen atoms, or benzo-fused 5-membered heteroaryl bonded via nitrogen and containing 1 to 3 nitrogen atoms: 5-membered heteroaryl ring groups which, in addition to carbon atoms, may contain 1 to 4 nitrogen atoms or 1 to 3 nitrogen atoms, respectively, as ring members and in which 2 adjacent carbon ring members or one nitrogen and one adjacent carbon ring member may be bridged by a buta-1,3-diene-1,4-diyl group, these rings being bonded to the skeleton via one of the nitrogen ring members;

6-membered heteroaryl containing 1 to 3, or 1 to 4, nitrogen atoms: 6-membered heteroaryl ring groups which, in addition to carbon atoms, may contain 1 to 3, or 1 to 4, respectively, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl containing 1 to 4 nitrogen atoms: 6-membered heteroaryl ring groups in which 2 adjacent carbon ring members may be bridged by a buta-1,3-diene-1,4-diyl group, eg. quinoline, isoquinoline, quinazoline and quinoxaline.

Preferred with a view to the fungicidal action against harmful fungi, eg. *Pyricularia oryzae*, are cycloalkylalkanecarboxamides I with the following substituents, the preference existing in each case alone or in combination:

The carbon atom which has attached to it the groups $R^1$ and $R^2$ is preferably in the R configuration.

Preferred cycloalkylalkanecarboxamides I are those where $R^1$ is methyl and $R^2$ is either methyl or hydrogen; especially preferred are compounds I where $R^1$ is methyl and $R^2$ is hydrogen.

Further preferred cycloalkanecarboxamides [sic] of the formula I are those where W is unsubstituted or substituted phenyl which is substituted in particular in the 2-position or in the positions 2 and 4. Very specially preferred is substitution in the 4-position on the phenyl ring and preferably here substitution by cyano or methoxy, by preference substitution by methyl and, in particular, by halogen, chlorine again being preferred here.

Additionally, preference is given to cycloalkanecarboxamides of the formula I where W is 1- or 2-naphthyl which is in each case unsubstituted or substituted by one to three of the following groups: halogen, cyano, $C_1$–$C_4$-alkyl or $C_1$–$C_4$-alkoxy. Particular preference is given to unsubstituted 1- or 2-naphthyl or 2-naphthyl which carries one of the following groups: chlorine, cyano, methyl or methoxy. Unsubstituted 2-naphthyl is particularly preferred.

Moreover, preferred cycloalkylalkanecarboxamides I are those where n=1. The substituents $R^3$ and $R^4$ are by preference $C_1$–$C_4$-alkyl and in particular methyl or ethyl. Also preferred is the combination in which one of the two substituents is hydrogen and the other one is $C_1$–$C_4$-alkyl, in particular methyl or ethyl.

Furthermore preferred are α-chloro or α-bromocycloalkylalkanecarboxamides I (Y=bromine or chlorine). Especially preferred are α-cyanocycloalkylalkanecarboxamides I (Y=cyano).

Furthermore, preference is given to cycloalkylalkanecarboxamides of the formula I where A is a substituted $C_3$–$C_6$-cycloalkyl. Particular preference is given to a methylated $C_3$–$C_6$-cycloalkyl radical which preferably carries the methyl substituent at the carbon linking the cycloalkane ring with the rest of the molecule.

Finally, preferred cycloalkylalkanecarboxamides of the general formula I are those where A is unsubstituted or substituted cyclopropyl. In particular, cyclopropyl which has attached to it one to three substituents selected from the group consisting of chlorine and $C_1$–$C_3$-alkyl, in particular methyl, is preferred. By preference, chlorinated cyclopropyl has attached to the cyclopropane ring two chlorine atoms in geminal position. By preference, alkylated or, preferably, methylated, cyclopropyl has one of the alkyl (methyl) substituents attached to the carbon atom at the site where the cyclopropane ring is linked to the remaining moiety.

Especially preferred with a view to their use are the compounds I compiled in the tables below.

TABLE 1

Carboxamides Ia.001 to Ia.108 of the formula Ia
(* = configuration of the atom designated "*";
R = R configuration; S = S configuration; rac. = racemic)

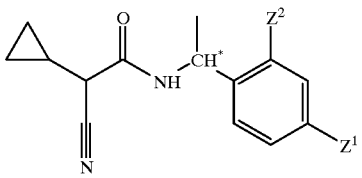

Ia

| No. | $Z^1$ | $Z^2$ | * |
|---|---|---|---|
| Ia.001 | H | H | R |
| Ia.002 | H | H | S |
| Ia.003 | H | H | rac. |
| Ia.004 | H | Cl | R |
| Ia.005 | H | Cl | S |
| Ia.006 | H | Cl | rac. |
| Ia.007 | H | $CH_3$ | R |
| Ia.008 | H | $CH_3$ | S |
| Ia.009 | H | $CH_3$ | rac. |
| Ia.010 | H | $OCH_3$ | R |
| Ia.011 | H | $OCH_3$ | S |
| Ia.012 | H | $OCH_3$ | rac. |
| Ia.013 | H | F | R |
| Ia.014 | H | F | S |
| Ia.015 | H | F | rac. |
| Ia.016 | H | CN | R |
| Ia.017 | H | CN | S |
| Ia.018 | H | CN | rac. |
| Ia.019 | Cl | H | R |
| Ia.020 | Cl | H | S |
| Ia.021 | Cl | H | rac. |
| Ia.022 | Cl | Cl | R |
| Ia.023 | Cl | Cl | S |

TABLE 1-continued

Carboxamides Ia.001 to Ia.108 of the formula Ia
(* = configuration of the atom designated "*";
R = R configuration; S = S configuration; rac. = racemic)

Ia

| No. | $Z^1$ | $Z^2$ | * |
|---|---|---|---|
| Ia.024 | Cl | Cl | rac. |
| Ia.025 | Cl | $CH_3$ | R |
| Ia.026 | Cl | $CH_3$ | S |
| Ia.027 | Cl | $CH_3$ | rac. |
| Ia.028 | Cl | $OCH_3$ | R |
| Ia.029 | Cl | $OCH_3$ | S |
| Ia.030 | Cl | $OCH_3$ | rac. |
| Ia.031 | Cl | F | R |
| Ia.032 | Cl | F | S |
| Ia.033 | Cl | F | rac. |
| Ia.034 | Cl | CN | R |
| Ia.035 | Cl | CN | S |
| Ia.036 | Cl | CN | rac. |
| Ia.037 | $CH_3$ | H | R |
| Ia.038 | $CH_3$ | H | S |
| Ia.039 | $CH_3$ | H | rac. |
| Ia.040 | $CH_3$ | Cl | R |
| Ia.041 | $CH_3$ | Cl | S |
| Ia.042 | $CH_3$ | Cl | rac. |
| Ia.043 | $CH_3$ | $CH_3$ | R |
| Ia.044 | $CH_3$ | $CH_3$ | S |
| Ia.045 | $CH_3$ | $CH_3$ | rac. |
| Ia.046 | $CH_3$ | $OCH_3$ | R |
| Ia.047 | $CH_3$ | $OCH_3$ | S |
| Ia.048 | $CH_3$ | $OCH_3$ | rac. |
| Ia.049 | $CH_3$ | F | R |
| Ia.050 | $CH_3$ | F | S |
| Ia.051 | $CH_3$ | F | rac. |
| Ia.052 | $CH_3$ | CN | R |
| Ia.053 | $CH_3$ | CN | S |
| Ia.054 | $CH_3$ | CN | rac. |
| Ia.055 | $OCH_3$ | H | R |
| Ia.056 | $OCH_3$ | H | S |
| Ia.057 | $OCH_3$ | H | rac. |
| Ia.058 | $OCH_3$ | Cl | R |
| Ia.059 | $OCH_3$ | Cl | s |
| Ia.060 | $OCH_3$ | Cl | rac. |
| Ia.061 | $OCH_3$ | $CH_3$ | R |
| Ia.062 | $OCH_3$ | $CH_3$ | S |
| Ia.063 | $OCH_3$ | $CH_3$ | rac. |
| Ia.064 | $OCH_3$ | $OCH_3$ | R |
| Ia.065 | $OCH_3$ | $OCH_3$ | S |
| Ia.066 | $OCH_3$ | $OCH_3$ | rac. |
| Ia.067 | $OCH_3$ | F | R |
| Ia.068 | $OCH_3$ | F | S |
| Ia.069 | $OCH_3$ | F | rac. |
| Ia.070 | $OCH_3$ | CN | R |
| Ia.071 | $OCH_3$ | CN | S |
| Ia.072 | $OCH_3$ | CN | rac. |
| Ia.073 | F | H | R |
| Ia.074 | F | H | S |
| Ia.075 | F | H | rac. |
| Ia.076 | F | Cl | R |
| Ia.077 | F | Cl | S |
| Ia.078 | F | Cl | rac. |
| Ia.079 | F | $CH_3$ | R |
| Ia.080 | F | $CH_3$ | S |
| Ia.081 | F | $CH_3$ | rac. |
| Ia.082 | F | $OCH_3$ | R |
| Ia.083 | F | $OCH_3$ | s |
| Ia.084 | F | $OCH_3$ | rac. |
| Ia.085 | F | F | R |
| Ia.086 | F | F | S |

TABLE 1-continued

Carboxamides Ia.001 to Ia.108 of the formula Ia
(* = configuration of the atom designated "*";
R = R configuration; S = S configuration; rac. = racemic)

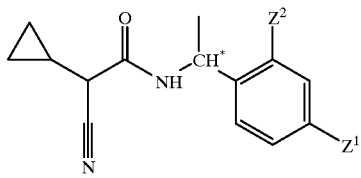

Ia

| No. | Z¹ | Z² | * |
|---|---|---|---|
| Ia.087 | F | F | rac. |
| Ia.088 | F | CN | R |
| Ia.089 | F | CN | S |
| Ia.090 | F | CN | rac. |
| Ia.091 | CN | H | R |
| Ia.092 | CN | H | S |
| Ia.093 | CN | H | rac. |
| Ia.094 | CN | Cl | R |
| Ia.095 | CN | Cl | S |
| Ia.096 | CN | Cl | rac. |
| Ia.097 | CN | CB3 | R |
| Ia.098 | CN | CH₃ | S |
| Ia.099 | CN | CH₃ | rac. |
| Ia.100 | CN | OCH₃ | R |
| Ia.101 | CN | OCH₃ | S |
| Ia.102 | CN | OCH₃ | rac. |
| Ia.103 | CN | F | R |
| Ia.104 | CN | F | S |
| Ia.105 | CN | F | rac. |
| Ia.106 | CN | CN | R |
| Ia.107 | CN | CN | S |
| Ia.108 | CN | CN | rac. |

TABLE 2

Carboxamides Ib.001 to Ib.108 of the formula Ib in which the meanings of the combinations of Z¹, Z² and "*" are indicated by the lines of Table 1.

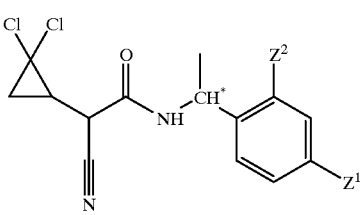

Ib

TABLE 3

Carboxamides Ic.001 to Ic.108 of the formula Ic in which the meanings of the combinations of Z¹, Z² and "*" are indicated by the lines of Table 1.

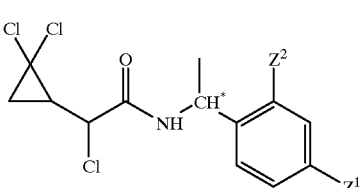

Ic

TABLE 4

Carboxamides Id.001 to Id.108 of the formula Id in which the meanings of the combinations of Z¹, Z² and "*" are indicated by the lines of Table 1.

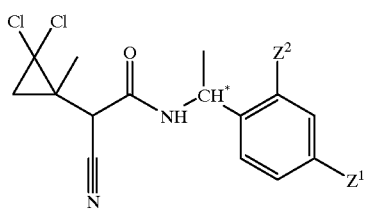

Id

TABLE 5

Carboxamides Ie.001 to Ie.108 of the formula Ie in which the meanings of the combinations of Z¹, Z² and "*" are indicated by the lines of Table 1.

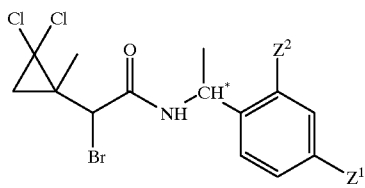

Ie

TABLE 6

Carboxamides If.001 to If.108 of the formula If in which the meanings of the combinations of Z¹, Z² and "*" are indicated by the lines of Table 1.

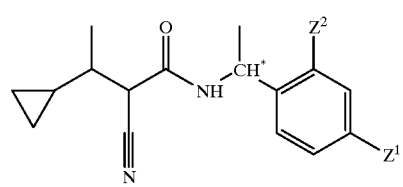

If

TABLE 7

Carboxamides Ig.001 to Ig.108 of the formula Ig in which the meanings of the combinations of Z¹, Z² and "*" are indicated by the lines of Table 1.

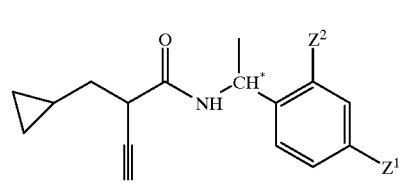

Ig

TABLE 8

Carboxamides Ih.001 to Ih.108 of the formula Ih in which the meanings of the combinations of $Z^1$, $Z^2$ and "*" are indicated by the lines of Table 1.

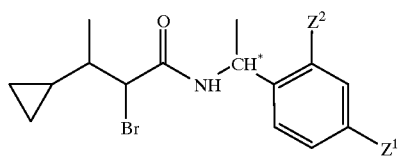

Ih

TABLE 9

Carboxamides Ii.001 to Ii.108 of the formula Ii in which the meanings of the combinations of $Z^1$, $Z^2$ and "*" are indicated by the lines of Table 1.

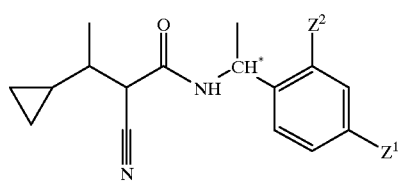

Ii

TABLE 10

Carboxamides Ik.001 to Ik.108 of the formula Ik in which the meanings of the combinations of $Z^1$, $Z^2$ and "*" are indicated by the lines of Table 1.

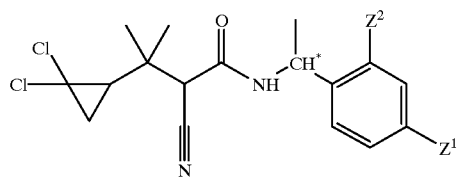

Ik

TABLE 11

Carboxamides Im.001 to Im.108 of the formula Im in which the meanings of the combinations of $Z^1$, $Z^2$ and "*" are indicated by the lines of Table 1.

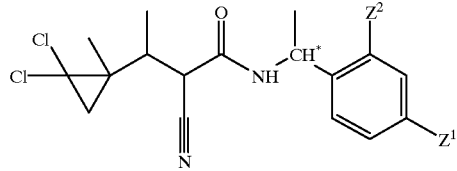

Im

TABLE 12

Carboxamides In.001 to In.108 of the formula In in which the meanings of the combinations of $Z^1$, $Z^2$ and "*" are indicated by the lines of Table 1.

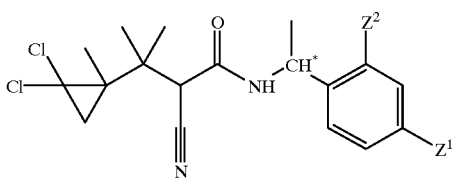

In

TABLE 13

Carboxamides Io.001 to Io.108 of the formula In [sic] in which the meanings of the combinations of $Z^1$, $Z^2$ and "*" are indicated by the lines of Table 1.

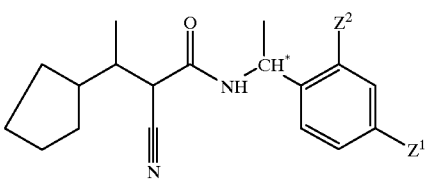

Io

TABLE 14

Carboxamides Ip.001 to Ip.108 of the forinula Ip in which the meanings of the combinations of $Z^1$, $Z^2$ and "*" are indicated by the lines of Table 1.

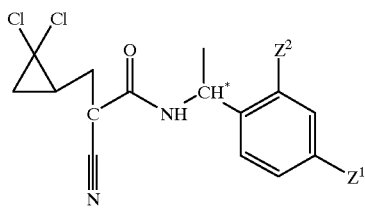

Ip

TABLE 15

Carboxamides Iq.001 to Iq.108 of the formula Iq in which the meanings of the combinations of $Z^1$, $Z^2$ and "*" are indicated by the lines of Table 1.

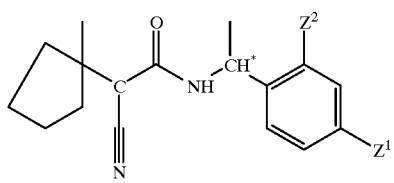

Iq

Moreover, processes have been found with which the carboxamides I can be prepared in good yields.

TABLE 16

Carboxamides Ir.001 to Ir.108 of the formula Ir in which the ineanings of the combinations of $Z^1$, $Z^2$ and "*" are indicated by the lines of Table 1.

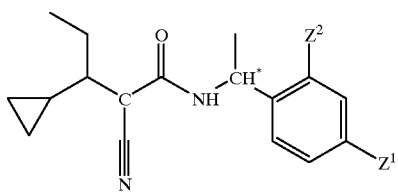

Ir

TABLE 17

Carboxamides Is.001 to Is.1OB of the formula Is in which the meanings of the combinations of $Z^1$, $Z^2$ and "*" are indicated by the lines of Table 1.

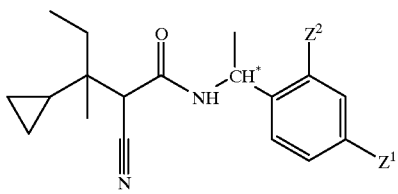

Is

TABLE 18

Carboxamides It.001 to It.108 of the formula It in which the meanings of the combinations of $Z^1$, $Z^2$ and "*" are indicated by the lines of Table 1.

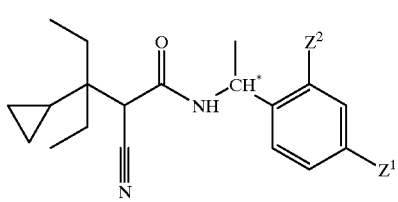

It

TABLE 19

Carboxarnides Iu.001 to Iu.108 of the formula Iu in which the meanings of the combinations of $Z^1$, $Z^2$ and "*" are indicated by the lines of Table 1.

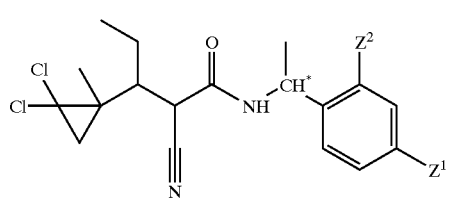

Iu

TABLE 20

Carboxamides Iv.1 to Iv.24 of the formula Iv (the configuration of the atom labeled "*" is racemic)

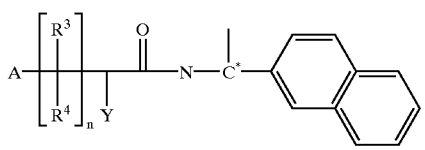

Iv

| No. | A | n | $R^3$ | $R^4$ | Y |
|---|---|---|---|---|---|
| Iv.1 |  | 0 | — | — | CN |
| Iv.2 | 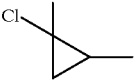 | 0 | — | — | CN |
| Iv.3 | 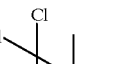 | 0 | — | — | CN |
| Iv.4 | 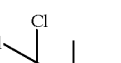 | 0 | — | — | Cl |
| Iv.5 |  | 0 | — | — | Br |
| Iv.6 |  | 0 | — | — | CN |
| Iv. 7 | 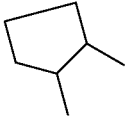 | 0 | — | — | CN |
| Iv.8 |  | 1 | H | H | CN |
| Iv.9 |  | 1 | $CH_3$ | H | CN |
| Iv.10 |  | 1 | $CH_3$ | H | Br |
| Iv.11 |  | 1 | $CH_3$ | $CH_3$ | CN |
| Iv.12 |  | 1 | $C_5H_5$ | H | CN |
| Iv.13 |  | 1 | $C_5H_5$ | $CH_3$ | CN |

TABLE 20-continued

Carboxamides Iv.1 to Iv.24 of the formula Iv
(the configuration of the atom labeled "*" is racemic)

Iv $$A\text{---}\left[\begin{array}{c}R^3\\|\\|\\R^4\end{array}\right]_n\!\!\!\begin{array}{c}O\\\|\\C\\|\\Y\end{array}\!\!\!\text{---}N\text{---}\overset{|}{\underset{|}{C^*}}\text{---}\!\!\!\begin{array}{c}\text{naphthyl}\end{array}$$

| No. | A | n | $R^3$ | $R^4$ | Y |
|---|---|---|---|---|---|
| Iv.14 | cyclopropyl | 1 | $C_5H_5$ | $C_5H_5$ | CN |
| Iv.15 | dichlorocyclopropyl | 1 | H | H | CN |
| Iv.16 | dichlorocyclopropyl | 1 | $CH_3$ | H | CN |
| Iv.17 | dichlorocyclopropyl | 1 | $CH_3$ | $CH_3$ | CN |
| Iv.18 | dichlorocyclopropyl | 1 | $C_5H_5$ | H | CN |
| Iv.19 | dichlorocyclopropyl | 1 | $CH_3$ | H | CN |
| Iv.20 | dichlorocyclopropyl | 1 | $CH_3$ | $CH_3$ | CN |
| Iv.21 | dichlorocyclopropyl | 1 | $C_5H_5$ | H | CN |
| Iv.22 | dichlorocyclopropyl | 1 | $C_5H_5$ | $CH_3$ | CN |
| Iv.23 | cyclopentyl | 1 | $CH_3$ | H | CN |
| Iv.24 | cyclopentyl | 1 | $CH_3$ | H | CN |

TABLE 21

Carboxamides Iw.1 to Iw.24 of the formula Iw in which the meanings of the combinations of A, n, $R^3$, $R^4$ and Y are indicated by the lines of Table 20.

(the configuration of the atom labeled "*" is R)

Iw $$A\text{---}\left[\begin{array}{c}R^3\\|\\|\\R^4\end{array}\right]_n\!\!\!\begin{array}{c}O\\\|\\C\\|\\Y\end{array}\!\!\!\text{---}N\text{---}\overset{|}{\underset{|}{C^*}}\text{---}\!\!\!\begin{array}{c}\text{2-naphthyl}\end{array}$$

TABLE 22

Carboxamides Iz.1 to Iz.24 of the formula Iz in which the meanings of the combinations of A, n, $R^3$, $R^4$ and Y are indicated by the lines of Table 20.

(the configuration of the atom labeled "*" is racemic)

Iz $$A\text{---}\left[\begin{array}{c}R^3\\|\\|\\R^4\end{array}\right]_n\!\!\!\begin{array}{c}O\\\|\\C\\|\\Y\end{array}\!\!\!\text{---}N\text{---}\overset{|}{\underset{|}{C^*}}\text{---}\!\!\!\begin{array}{c}\text{1-naphthyl}\end{array}$$

According to a process which is preferred in accordance with the invention, the carboxamides I

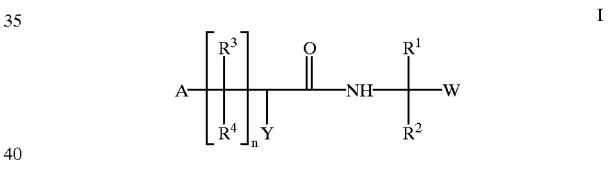

are obtained by reacting the carboxylic acid derivatives II

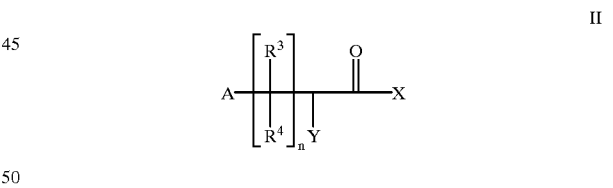

with amines of the formula III

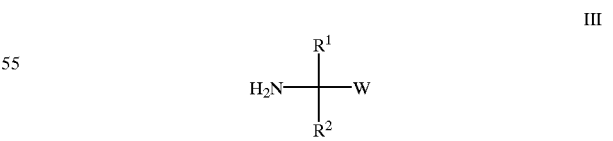

Amide formation is effected by the processes known from the literature. In the processes, the free carboxylic acid of the formula II' where X is hydroxyl are, as a rule, previously converted into an activated carboxylic acid derivative II where X is, for example, chlorine.

Activation of the carboxylic acid II' can preferably also be effected in situ by the direct use of the carboxylic acid II' with addition of, for example, dicyclohexylcarbodiimide, ethyl chloroformate, diethyl cyanophosphonate, triphenylphosphine/azodicarboxylic ester, 2-pyridine disulfide/triphenylphosphine, carbonyldiimidazole, thionyl chloride, phosphorus trichloride, phosphorus pentachloride, and the like. In general, the, for example, carbodiimides are added in equimolar amounts based on the carboxylic acids II'.

Activation of the carboxylic acids via acyl cyanides is effected for example for reacting the carboxylic acids II' with diethyl cyanophosphonate, preferably in an inert solvent such as tetrahydrofuran, toluene or dichloromethane (cf. Tetrahedron Lett. 18 (1973) 1595–8).

Activation via anhydrides is effected for example by reacting the carboxylic acids II' with carbonic acid chlorides, such as ethyl chloroformate, in general in the presence of bases and, if appropriate, in an inert solvent such as toluene or tetrahydrofuran (cf. "Houben-Weyl", 4th ed. (1974), 15/1, page 28–32).

Amide formation is preferably carried out in the presence of bases such as tertiary amines, eg. triethylamine or dimethylcyclohexylamine, alkali metal carbonates, alkali metal hydroxides, pyridine and the like. The reactants and the auxiliary base are expediently employed in equimolar amounts. A small excess of the auxiliary base of from 0.1–0.5 equivalents may be beneficial under certain circumstances.

Suitable solvents are aliphatic hydrocarbons such as hexane and ligroin, aromatic hydrocarbons such as toluene and xylene, chlorinated hydrocarbons such as methylene chloride and 1,2-dichloroethane, ethers such as methyl tert-butyl ether and tetrahydrofuran, polar aprotic solvents such as acetonitrile and dimethylformamide, or esters such as ethyl acetate, or mixtures of these.

The molar ratio of carboxylic acid derivatives II to amine III is generally from 0.8 to 1.5, preferably from 0.9 to 1.1.

After the reaction is complete, the mixture is worked up as usual, for example by introducing the reaction mixture into water followed by extraction of the amide.

Those amines of the formula III which are not already known can be obtained readily (cf. Organikum (1993) Barth Verlagsgesellschaft mbH Leipzig, p. 509 et seq.; "Houben-Weyl", volume 15/1, pages 648–665; J. Am. Chem. Soc. 58, (1936), 1808–1811, Indian J. Chem. 10 (1972), 366).

The R isomer can be separated from the racemates of the amines III in a manner known per se, for example by fractional crystallization using optically active tartaric acid or preferably by enzyme-catalyzed esterification and subsequent hydrolysis (cf. for example WO-A 95/08636).

The preparation of α-cyanocyclopropylacetic acid is described in Org. Prep. Proced. Int. 5 (1973), 25–29. Diagram 1 shows a general route for synthesizing carboxylic acids of the formula II' (cf. Collect. Czech. Chem. Commun. 48 (1983) 1597–1601 and J. Polym. Sci., Polym. Chem. Ed. 14 (1976) 2357–9).

Diagram 1

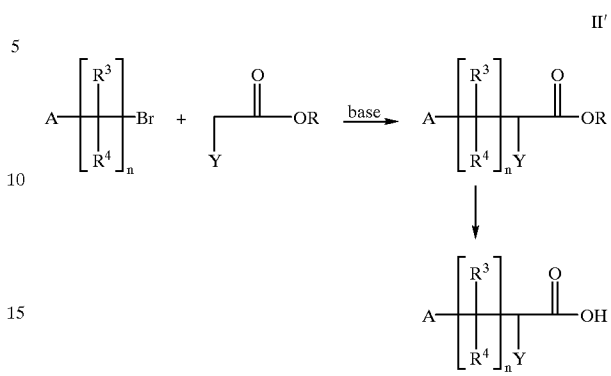

Furthermore, carboxylic acid derivatives of the formula IIA can be prepared in accordance with Diagram 2.

Diagram 2

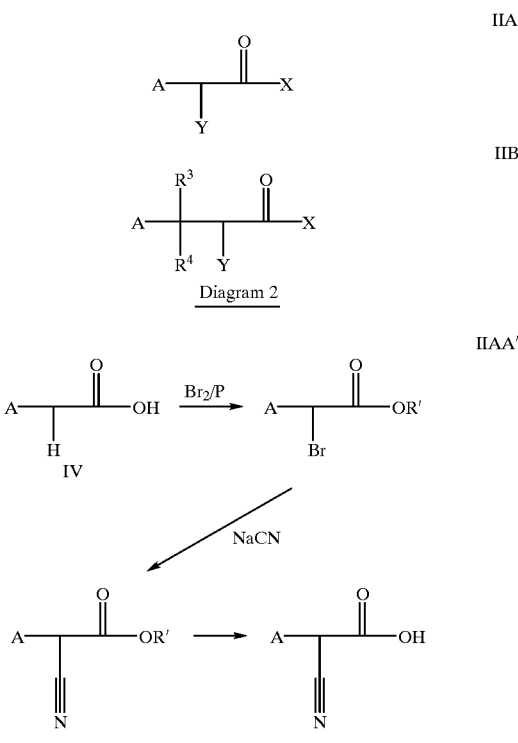

The cycloalkylacetic acids of the formula IV where A has the meaning in claim 1 are known (J. Chem. Technol. Biotechnol., Chem. Technol., 33A (1983) 109–15; NL 65 06 881; Chem. Ber. 41 (1908) 2627; Chem. Ber. 35 (1902) 2688).

The cycloalkylacetic acids IV can be brominated in the α position following the protocol described in J. Am. Chem. Soc. 70 (1948) 3626–7. Working-up in the presence of a $C_1$–$C_6$-alcohol leads directly to the corresponding ester. The subsequent bromine/cyano exchange is carried out as described in Synth. Commun. 23 (1993) 2323–9. Hydrolysis of the esters to the carboxylic acids IIAA' is carried out by standard methods (Organikum 1993 Barth Verlagsgesellschaft mbH, Leipzig, p. 431ff.).

The carboxylic acid derivatives of the formula IIB are accessible for example via the route shown in Diagram 3.

Diagram 3

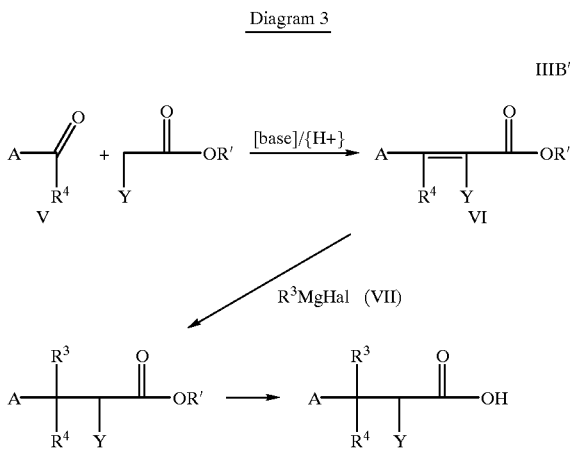

Diagram 4

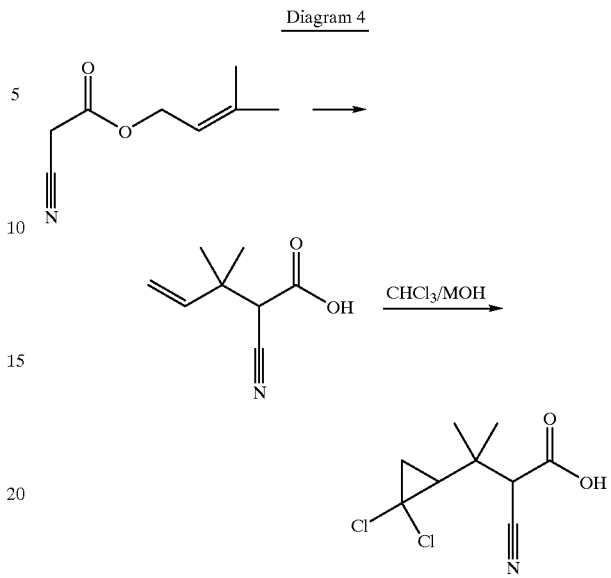

The starting materials, acyl- or formylcycloalkanes of the formula V, are generally accessible (cf., inter alia, J. Chem. Soc., Perkin Trans. I, 6 (1994) 739–52; EP-A 725 066). They are reacted with $C_1$–$C_6$-alkyl α-halo- or α-cyanoacetates in a Knoevenagel reaction to give the Michael systems VI (cf. Chem. Heterocycl. Compd. 24 (1988) 860–4).

Condensation is normally effected with a solvent which is not miscible with water, such as hexane, toluene or xylene, while removing the water formed during the reaction. To this end, the reaction mixture is boiled under reflux for several hours.

The catalysts used are bases, eg. piperidine, pyridine, ammonia or β-alanine, in the presence of an acid, for example glacial acetic acid.

An alkyl Grignard compound of the formula VII where $R^3$ has the meaning given in claim 1 and Hal is chlorine, bromine or iodine is subsequently subjected to an addition reaction with a Michael systems [sic] of the formula VI to obtain saturated systems of the type IIB.

The reaction is carried out under solvents which are inert under reaction conditions. Particularly preferred are ethers such as tetrahydrofuran, diethyl ether, dimethoxyethane or methyl tert-butyl ether. As a rule, the reaction temperature is set at from −10 to 80° C. and preferably from 10 to 60° C.

As a rule, the Grignard compound VII is employed in an equimolar amount based on the Michael system VI. In some cases it proves advantageous to employ the Grignard compound in an excess of from 0.2 to 0.5 mol equivalents.

As a rule, the addition reaction is carried out with copper catalysts by adding 1–10 mol % of, for example, copper(I) iodide. This results in a higher selectivity regarding the 1,2-addition versus the 1,4-addition.

Finally, the free carboxylic acids IIB' are prepared by subjecting the corresponding esters to alkaline hydrolysis (Organikum 1993 Barth Verlagsgesellschaft mbH, Leipzig, p. 431 et seq.).

A sophisticated route to obtain 2-cyano-3-(2,2-dichlorocyclopropyl)-3-methylbutanoic acid is proposed in Diagram 4.

The preparation of 2-cyano-3,3-dimethylpent-4-enoic acid from 3-methylbut-2-enyl cyanoacetate is described in DE-A 26 49 711 and Res. Discl. (1985) 249,55. 2-Cyano-3-(2,2-dichlorocyclopropyl)-3-methylbutanoic acid can be obtained directly by an addition reaction with dichlorocarbene, which is accessible from chloroform and alkali metal hydroxides by means of standard processes. To improve the yield, it is expedient to protect the carboxylic acid function before the cyclopropanation step (for example by converting it into the tert-butyl ester).

The abovementioned processes allow access to carboxylic acid derivatives II which are suitable for example for preparing the carboxamides I according to the invention.

The specially preferred embodiments of the carboxylic acid derivatives II with respect to the substituents $R^3$, $R^4$, A and Y correspond to those of the carboxamides I.

X represents a nucleophilically exchangeable radical such as hydroxyl, $C_1$–$C_4$-alkoxy, halogen eg. bromine or chlorine, hetaryl, eg. imidazolyl or pyridyl, carboxylate, eg. acetate or trifluoroacetate, and the like.

Particularly preferred are carboxylic acid derivatives of the formula II where n is 1 and/or is unsubstituted or substituted cyclopropyl. In the event that n is 0, preferred carboxylic acid derivatives of the formula IIA are those where A is cyclopropyl which may have attached to it from 1 to 3 substituents, eg. chlorine and/or $C_1$–$C_3$-alkyl. Chlorinated cyclopropyl preferably has attached to it two chlorine atoms, and these in the geminal position on the cyclopropane ring.

The compounds I are distinguished by an outstanding activity against a broad spectrum of phytopathogenic fungi, in particular from the classes of the Ascomycetes, Basidiomycetes, Deuteromycetes and Phycomycetes. Some of them act systemically and they can be employed in crop protection as foliar- and soil-acting fungicides.

They are especially important for controlling a large number of fungi on a variety of crop plants such as wheat, rye, barley, oats, rice, maize, grass, bananas, cotton, soybeans, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, ornamentals, vegetables and grapevines, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines, Pseudoperonospera [sic] species in hops and cucumbers, Alternaria species on vegetables and fruit, and Mycosphaerella species in bananas.

Moreover, the compounds I are suitable for controlling harmful fungi in the protection of materials (eg. wood, paper, dispersions for paint, fibers or fabrics) and in the protection of stored products.

The compounds I are applied by treating the fungi or the plants, seeds, materials or the soil to be protected against fungal infection with a fungicidally reactive amount of the active ingredients. Application is effected before or after infection of the materials, plants or seeds by the fungi.

They can be converted into customary formulations, such as solutions, emulsions, suspensions, dusts, powders, pastes and granules. The use form depends on the intended purpose; in any case, it should guarantee fine and uniform distribution of the compound according to the invention. The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries are essentially: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers, such as non-ionic and anionic emulsifiers (eg. polyoxyethylene fatty alcohol ethers, alkylsulfonates and arylsulfonates) and dispersants such as lignin-sulfite waste liquors and methylcellulose.

In general, the fungicidal compositions comprise from 0.1 to 95% by weight, preferably from 0.5 to 90% by weight of active ingredient.

Depending on the nature of the desired effect, the application rates are from 0.01 to 2.0 kg of active ingredient per ha when used in crop protection.

In the treatment of seeds, amounts of from 0.001 to 0.1 g, preferably from 0.01 to 0.05 g, of active ingredient are generally required per kilogram of seed.

When used in the protection of materials or stored products, the rate of application of the active ingredient depends on the nature of the field of application and of the desired effect. For example, normal rates of application in the protection of materials are from 0.001 g to 2 kg, preferably 0.005 g to 1 kg, of active ingredient per cubic meter of treated material.

In their use form as fungicides, the compositions according to the invention can also be present together with other active ingredients, eg. with herbicides, insecticides, growth regulators, fungicides or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc [N,N-ethylenebisdithiocarbamate], ammonia complex of zinc [N,N'-propylenebisdithiocarbamate], zinc [N,N'-propylenebisdithiocarbamate], N,N'-polypropylenebis(thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoximino-[α-(2-phenoxyphenyl)]acetamide, N-methyl-E-methoximino-[α-(2,5-dimethylphenoxy)-o-tolyl]acetamide, anilinopyrimidines such as N-(4,6-dimethylpyrimidin-2-yl)aniline, N-(4-methyl-6-(1-propynyl)pyrimidin-2-yl]aniline, N-(4-methyl-6-cyclopropylpyrimidin-2-yl) aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acryloylmorpholine, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methyl-silyl)methyl)-1H-1,2,4-triazole.

The active ingredients can be applied as such in the form of their formulations or in the form of the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they should guarantee the finest possible distribution of the active ingredients according to the invention.

The active ingredient concentrations in the ready-to-use preparations can be varied within substantial ranges.

They are in general from 0.0001 to 10%, preferably from 0.01 to 1%.

The active ingredients can also be used successfully in the ultra-low-volume method (ULV), it being possible to apply formulations with over 95% by weight of active ingredient, or even the active ingredient without additives.

The rate of application of active ingredient for controlling pests is from 0.1 to 2.0, preferably from 0.2 to 1.0, kg/ha under field conditions.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable and animal origin, aliphatic, cycloaliphatic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone or water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active ingredient, wetting agent, tackifier, dispersant or emulsifier and, if desired, solvent or oil, and these concentrates are suitable for dilution with water.

Suitable surfactants are alkali metal salts, alkaline earth metal salts and ammonium salts of lignosulfonic acid, naphthalenesulfonic acid, phenolsulfonic acid, dibutylnaphthalenesulfonic acid; alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether, ethoxylated polyoxypropylene, lauryl alcohol polyglycol ether acetal, sorbitol esters, lignin-sulfite waste liquors and methylcellulose.

Powders, materials for spreading and dusts can be prepared by mixing or concomitantly grinding the active ingredients with a solid carrier.

In general, the formulations comprise from 0.01 to 95% by weight, preferably from 0.1 to 90% by weight, of the active ingredients. The active ingredients are employed in a purity of from 90% to 100%, preferably 95% to 100% (according to NMR spectrum).

Examples of formulations are:

I. 5 parts by weight of a compound according to the invention mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesive properties (active ingredient content 23% by weight).

III. 10 parts by weight of a compound according to the invention are dissolved in a mixture which is composed of 90 parts by weight of xylene, 6 parts by weight of the adduct of 8 to 10 mol of ethylene oxide and 1 mol of oleic acid N-monoethanolamide, 2 parts by weight of calcium dodecylbenzene sulfonate and 2 parts by weight of the adduct of 40 mol of ethylene oxide and 1 mol of castor oil (active ingredient content 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-alpha-sulfonamide, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone; this gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredient to solid carriers. Examples of solid carriers are mineral earths, such as silica gel [sic], silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas and products of vegetable origin such as cereal meal, tree bark meal, wood meal and nutshell meal, cellulose powders and other solid carriers.

Various types of oils, or herbicides, fungicides, other pesticides, or bactericides may be added to the active ingredients, if appropriate also only just prior to use (tank mix). These agents can be admixed with compositions according to the invention in a weight ratio of 1:10 to 10:1.

SYNTHESIS EXAMPLES

Preparation of the carboxylic Acid Derivatives II

Example 1

1-Cyano-1-(2,2-dichloro-1-methylcyclopropyl)acetic acid (Comp. II.1 in Table A)

a) Ethyl 1-bromo-1-(2,2-dichloro-1-methylcyclopropyl)acetate 1-(2,2-Dichloro-1-methylcyclopropyl)acetic acid (cf. in this context J. Chem. Technol. Biotechnol. Chem. Technol. Vol. 33A, (1983), 109–15) was reacted in a accordance with the protocol in J. Am. Chem. Soc. 70, (1948), pages 3626–7, to give ethyl 1-bromo-1-(2,2-dichloro-1-methylcyclopropyl)acetate.

b) Ethyl 1-cyano-1-(2,2-dichloro-1-methylcyclopropyl)acetate

Bromine was exchanged for cyano by a protocol similar to Synth. Commun. 23, (1993), pages 2323–9.

c) 1-Cyano-1-(2,2-dichloro-1-methylcyclopropyl)acetic acid

The ester was hydrolyzed by refluxing ethyl 1-cyano-1-(2,2-dichloro-1-methylcyclopropyl)acetate for 4 hours in a mixture of equal parts of methanol, tetrahydrofuran and 2 N sodium hydroxide solution. For working-up, the same volume of 2 N sodium hydroxide solution was added, and the mixture was repeatedly extracted with diethyl ether. The aqueous phase was subsequently acidified by adding hydrochloric acid and also extracted with ether. Drying and concentrating this organic phase gave the title compound.

Example 2

1-Cyano-1-(2,2-dichlorocyclopropyl)acetic acid (Comp. II.2 in Table A)

a) Ethyl 1-bromo-1-(2,2-dichlorocyclopropyl)acetate 1-(2,2-Dichlorocyclopropyl)acetic acid (cf., in this context, NL 6506881) was reacted in accordance with the protocol in J. Am. Chem. Soc. Vol. 70, (1948), pages 3626–7 to give ethyl 1-bromo-1-(2,2-dichlorocyclopropyl)acetate.

b) Ethyl 1-cyano-1-(2,2-dichlorocyclopropyl)acetate

Bromine was exchanged for cyano by a protocol similar to Synth. Commun. 23, (1993), pages 2323–9.

c) 1-Cyano-1-(2,2-dichlorocyclopropyl)acetic acid

The ester was hydrolyzed by a method similar to Example 1c).

Example 3

2-Cyano-3-cyclopropylbutanoic acid (Comp. II.3 in Table A)

a) Ethyl 2-cyano-3-cyclopropyl-2-propenoate

A solution of 14 g (0.2 mol) of cyclopropylcarbaldehyde, 22.6 g (0.2 mol) of ethyl cyanoacetate, 1.4 ml of glacial acetic acid and 0.4 ml of piperidine in 200 ml of toluene was refluxed for 6 hours. After cooling, the mixture was washed with in each case 300 ml of 10% strength hydrochloric acid and water. The organic phase was dried and concentrated and the residue was subjected to distillation in vacuo. This gave 14.2 g (yield 43%) of ethyl 2-cyano-3-cyclopropyl-2-propenoate (b.p. 95° C./0.3 mbar).

b) Ethyl 2-cyano-3-cyclopropylbutanoate 7.3 g (44 mmol) of ethyl 2-cyano-3-cyclopropyl-2-propenoate and 0.15 g of copper(I) iodide were introduced into 100 ml of dry diethyl ether. 16.9 ml of etheric 3 M methylmagnesium bromide solution (51 mmol) was then added dropwise at reflux temperature, and the mixture was subsequently stirred for 14 hours at room temperature. For working-up, the mixture was poured into 300 ml of ice-water and stirred for 10 minutes. The aqueous phase was separated off and washed with ether. The combined organic phase [sic] were washed with saturated sodium chloride solution, dried with sodium sulfate and concentrated. The residue was subjected to fractional distillation in vacuo. This gave 4.9 g (yield 61%) of ethyl 2-cyano-3-cyclopropylbutanoate (b.p. 90° C./2 mbar).

c) 2-Cyano-3-cyclopropyl-butanoic acid 39.8 g (0.22 mol) of ethyl 2-cyano-3-cyclopropylbutanoic acid were refluxed for 4 hours in a mixture of in each case 150 ml of methanol, tetrahydrofuran and 2 N sodium hydroxide solution. For working-up, 200 ml of 2 N sodium hydroxide solution were added and the mixture was extracted repeatedly with diethyl ether. The aqueous phase was subsequently acidified by adding hydrochloric acid and also extracted with ether. After this organic phase had been dried and concentrated, 29 g (yield 86%) of 2-cyano-3-cyclopropylbutanoic acid were obtained.

Example 4

2-Cyano-3-cyclopropyl-3-methylbutanoic Acid (Comp. II.4 in Table A)

a) Ethyl 2-cyano-3-cyclopropylbut-2-enoate

A solution of 118 g (1.4 mol) of cyclopropyl methyl ketone and 113 g (1 mol) of ethyl cyanoacetate was reacted by a method similar to Example 3a) to give 50 g (yield 29%) of ethyl 2-cyano-3-cyclopropylbut-2-enoate (b.p. 105° C./6 mbar).

b) Ethyl 2-Cyano-3-cyclopropyl-3-methylbutanoate 50 g (0.28 mol) of ethyl 2-cyano-3-cyclopropyl-3-methylprop-2-enoate and 1.7 g of copper(I) iodide were reacted by a method similar to Example 3b) to give 20 g (yield 37%) of ethyl 2-cyano-3-cyclopropyl-3-methylbutanoate (b.p. 120° C./6 mbar).

c) 2-Cyano-3-cyclopropyl-3-methylbutanoic acid 20 g (0.1 mol) of ethyl 2-cyano-3-cyclopropyl-3-methylbutanoate were hydrolyzed by a method similar to Example 3c). This gave 13 g (yield 76%) of 2-cyano-3-cyclopropyl-3-methylbutanoic acid.

Example 5

2-Cyano-3-(2,2-dichloro-1-methylcyclopropyl)butanoic acid (Comp. II.5 in Table A)

a) Ethyl 2-cyano-3-(2,2-dichloro-1-methylcyclopropyl)prop-2-enoate 65.8 g (0.43 mol) of (2,2-dichloro-1-methylcylopropyl)carbaldehyde (cf., in this context, J. Chem. Soc., Perkin Trans. I, (1994), Vol. 6, pages 739–52) and 48.6 g (0.43 mol) of ethyl cyanoacetate were reacted by a method similar to Example 3a) and gave, after distillation, 63 g (yield 60%) of a pale yellow oil.

B.p. 95° C./0.8 mbar, $^1$H NMR (in CDCl$_3$): 1.4 (t, 3H); 1.64 (s, 3H); 1.8 (d, 1H); 2.04 (d, 1H); 4.3 (q, 2H); 7.8 (s, 1H)).

b) Ethyl 2-cyano-3-(2,2-dichloro-1-methylcyclopropyl)butanoate 5 g (20 mmol) of the ester obtained in Example 5a) were reacted by a method similar to Example 3b) to give 5 g (yield 95%) of ethyl 2-cyano-3-(2,2-dichloro-1-methylcyclopropyl)butanoate. B.p. 110° C./0.5 mbar.

c) 2-Cyano-3-(2,2-dichloro-1-methylcyclopropyl)butanoic acid 2 g (7.6 mmol) of the ester obtained in Example 5b) were hydrolyzed by a method similar to Example 3c) to give 1.7 g (yield 95%) of the acid as a brown oil.

Example 6

2-Cyano-3-(2,2-dichloroycyclopropyl)-3-methylbutanoic acid (Comp. II.6 in Table A)

2-Cyano-3,3-dimethylpent-4-enoic acid (cf., in this context, DE 2649711 and Res. Discl. (1985), 249, 55.) was cyclopropanized in accordance with the protocol in J. Chem. Technol. Biotechnol., Chem. Technol. (1983), Vol. 33A, 109–15.

Example 7

2-Cyano-3-(2,2-dichlorocyclopropyl)propionic acid (Comp. II.7 in Table A)

a) Ethyl 2-cyano-3-(2,2-dichlorocyclopropyl)propionate 4.5 g (39 mmol) of ethyl cyanoacetate and 9.6 g (47 mmol) of 1-bromo-1-(2,2-dichlorocyclopropyl)methane were initially charged under nitrogen in 26 ml of absolute ethanol. With stirring, 7.0 g of a 30% strength methanolic sodium methoxide solution were then added dropwise. The mixture was heated under reflux for 2 hours. After cooling to room temperature, the mixture was stirred overnight. The methanol was evaporated and the precipitated NaBr was completely dissolved by addition of water, with cooling to 10° C. The aqueous phase was extracted three times using methyl tert-butyl ether and the combined organic phases were then washed twice with water. The organic phase was dried using sodium sulfate, the solvent was removed and the crude product obtained as a residue was subjected to fractional distillation. This gave 2.4 g (26% yield) of ethyl 2-cyano-3-(2,2-dichlorocyclopropyl)propionate.

b) 2-Cyano-3-(2,2-dichlorocyclopropyl)propionic acid

The hydrolysis of the ester was carried out similarly to Example 1c).

Example 8

(1-Methylcyclopentyl)cyanoacetic acid (Compound II.8 in Table A)

a) Methyl cyanocyclopentylidineacetate

Similarly to Example 3a), a solution of 235 g (2.8 mol) of cyclopentanone and 198 g (2 mol) of methyl cyanoacetate was reacted to give 297 g (90% yield) of methyl cyanocyclopentylidine acetate. bp. 92° C./0.8 mbar.

b) Methyl (1-methylcyclopentyl)cyanoacetate

Similarly to Example 3b), 100 g (0.61 mol) of methyl cyanocyclopentylidineacetate and 0.7 g of copper (I) iodide were reacted to give 48 g (44% yield) of methyl (1-methylcyclopentyl)cyanoacetate. bp. 85° C./1.1 mbar.

c) (1-Methylcyclopentyl)cyanoacetic acid

Similarly to Example 3c), 48 g (0.26 mol) of methyl (1-methylcyclopentyl)cyanoacetate were hydrolyzed. This gave 44 g (100% yield) of (1-methylcyclopentyl)cyanoacetic acid.

Example 9

2-Cyano-3-cyclopropylpentanoic acid (Comp. II.9 in Table A)

a) Methyl 2-cyano-3-cyclopropylpent-2-enoate

Similarly to Example 3a), a solution of 4 g (40.8 mmol) of cyclopropyl ethyl ketone and 2.4 g (24 mmol) of methyl cyanoacetate was reacted to give 0.9 g (21% yield) of methyl 2-cyano-3-cyclopropylpent-2-enoate.

b) 2-Cyano-3-cyclopropylpentanoate

Under an atmosphere of nitrogen, 1 g (5.6 mmol) of the ester 9a) was initially charged in 10 ml of tetrahydrofuran and 5 ml of abs. methanol. After the addition of 0.3 g (5.6 mmol) of potassium borohydride, the mixture was stirred at room temperature overnight. For work-up, the mixture was hydrolyzed with water and acidified with 2N hydrochloric acid, and the aqueous phase was extracted with methyl tert-butyl ether. The combined organic phases were washed with water and saturated sodium chloride solution. The organic phases were dried using sodium sulfate and the solvent was removed, giving 0.6 g (60% yield) of methyl 2-cyano-3-cyclopropylpentanoate.

c) 2-Cyano-3-cyclopropylpentanoic acid

Similarly to Example 1c), 0.6 g of the ester 9b) was hydrolyzed. This gave 0.54 g (98% yield) of the title compound.

Example 10

2-Cyano-3-cyclopropyl-3-methylpentanoic acid (Comp. II.10 in Table A)

a) Methyl 2-cyano-3-cyclopropyl-3-methylpentanoate

Similarly to Example 3b), 1 g (5.6 mmol) of the ester 9a) was reacted. This gave 1.1 g of crude product which was used without any further purification.

b) 2-Cyano-3-cyclopropyl-3-methylpentanoic acid

Similarly to Example 1c), 0.5 g (2.56 mmol) of the ester 10a) was hydrolyzed. This gave 0.44 g (96% yield) of the title compound.

Preparation of the carboxamides I

Example 11

N-(4'-Chlorophenyl)ethyl-1-cyclopropyl-1-cyanoacetamide (Comp. I.1 in Table B)

The solution of 0.62 g (5 mmol) of 1-cyano-1-cyclopropylacetic acid (cf., in this context, Org. Prep. Proced. Int. (1973), Vol. 5, pp. 25–29) and 0.78 g (5 mmol) of racemic 1-(4-chlorophenyl)ethylamine in 50 ml of dichloromethane was treated with 0.5 g (5 mmol) of triethylamine. Then, 0.84 g of 93% strength (4.9 mmol) diethyl cyano-

TABLE A

II'

$$A\left[\begin{array}{c}R^3 \\ | \\ | \\ R^4\end{array}\right]_n \overset{|}{\underset{Y}{C}} - \overset{O}{\underset{}{C}} - OH$$

| No. | A | n | $R^3$ | $R^4$ | Y | Physical data (NMR in $CDCl_3$, data in ppm; m.p. in °C.) |
|---|---|---|---|---|---|---|
| II.1 | Cl,Cl-cyclopropyl | 0 | — | — | CN | |
| II.2 | Cl,Cl-cyclopropyl | 0 | — | — | CN | |
| II.3 | cyclopropyl | 1 | $CH_3$ | H | CN | $^{13}C$ NMR: 5; 14.6; 16; 40; 44; 67; 115; 170 |
| II.4 | cyclopropyl | 1 | $CH_3$ | $CH_3$ | CN | $^1H$ NMR: 0.3–0.6; 1.0; 3.4; 8.7 |
| II.5 | Cl,Cl-cyclopropyl | 1 | $CH_3$ | H | CN | $^{13}C$ NMR: 15; 33; 41; 67; 115; 170 |
| II.6 | Cl,Cl-cyclopropyl | 1 | $CH_3$ | $CH_3$ | CN | |
| II.7 | Cl,Cl-cyclopropyl | 1 | H | H | CN | $^1H$ NMR: 1.3; 1.8; 2.1–2.5; 3.8; 7.8 |
| II.8 | cyclopentyl | 0 | — | — | CN | $^1H$ NMR: 1.2; 1.5–1.9; 3.5; 9.2 |
| II.9 | cyclopropyl | 1 | $C_2H_5$ | H | CN | $^1H$ NMR: 0.3; 0.5–1.0; 1.3; 1.5–1.8; 1.9; 3.7; 7.5; |
| II.10 | cyclopropyl | 1 | $C_2H_5$ | $CH_3$ | CN | IR: 1056; 1203; 1386; 1463; 1721; 2884; 2928; 2967; 3087; 3174 | phosphonate was added dropwise at 10° C. and the mixture was stirred for 12 hours at room temperature. After 50 ml of dichloromethane were added, the mixture was washed with in each case 100 ml of 2 N sodium hydroxide solution, 5% strength hydrochloric acid and water. The organic phase was subsequently dried and concentrated. The residue which remained was purified by chromatography on silica gel (eluent:cyclohexane:tert-butyl methyl ether=7:3). 0.4 g (yield 32%) of the diastereomer mixture of the title compound remained as a solid residue of m.p. 117–20° C.

Example 12

N-(4'-chlorophenyl)ethyl 1-cyano-1-(2,2-dichloro-1-methylcyclopropyl)acetamide (Comp. I.4 in Table B)

The reaction of 1-cyano-1-(2,2-dichloro-1-methylcylopropyl)acetic acid with rac-1-(4-chlorophenyl)ethylamine analogously to Example 11 gave the title compound as a diastereomer mixture.

Example 13

N-(4'-Chlorophenyl)ethyl-1-cyano-1-(2,2-dichlorocyclopropyl)acetamide (Comp. I.5 in Table B)

The reaction of 1-cyano-1-(2,2-dichlorocylopropyl)acetic acid with racemic 1-(4-chlorophenyl)ethylamine analogously to Example 11 gave the title compound as a diastereomer mixture.

Example 14

N-(4'-Chlorophenyl)-(R)-ethyl-2-cyano-3-cyclopropylbutanamide (Comp. I.8 in Table B)

The reaction of 0.46 g (3 mmol) of 2-cyano-3-cyclopropylbutanoic acid and 0.47 g (3 mmol) of R-1-(4-chlorophenyl)ethylamine by a method similar to Example 11 gave 0.65 g (yield 75%) of the title compound as a colorless resin.

Example 15

N-(4'-Chlorophenyl)-(R)-ethyl-2-cyano-3-cyclopropyl-3-methylbutanamide (Comp. I.10 in Table B)

The reaction of 0.5 g (3 mmol) of 2-cyano-3-cyclopropyl-3-methylbutanoic acid with 0.47 g (3 mmol) of R-1-(4-chlorophenyl)ethylamine by a method similar to Example 11 gave, after chromatographic purification, 0.7 g (yield 80%) of the title compound (m.p. 103–6° C.).

Example 16

N-(4'-chlorophenyl)-(R)-ethyl-2-cyano-3-(2,2-dichloro-1-methylcyclopropyl)butanamide (Comp. I.12 in Table B)

The reaction of 2 g (8.5 mmol) of 2-cyano-3-(2,2-dichloro-1-methylcyclopropyl)butanoic acid with 1.3 g (8.5 mmol) of (R)-1-(4-chlorophenyl)ethylamine by a method similar to Example 11 gave the [sic] 3.1 g of the title compound (colorless resin) as a diastereomer mixture.

Example 17

N-(4'-Chlorophenyl)-(R)-ethyl-2-cyano-3-(2,2-dichlorocyclopropyl)-3-methylbutanamide (Comp. I.15 in Table B)

The reaction of the acid obtained in Example 6 with (R)-1-(4-chlorophenyl)ethylamine by a method similar to Example 11 gave the title compound as a diastereomer mixture.

Other cycloalkylalkanecarboxamides I which were, or can be, prepared in the same manner are listed in Table B:

TABLE B

| No. | A | n | R³ | R⁴ | Z | Y | * | Phys. data (NMR in CDCl₃, data in ppm; m.p. in ° C.) |
|---|---|---|---|---|---|---|---|---|
| I.1 | cyclopropyl | 0 | — | — | 4-Cl | CN | rac | m.p. 117–120 |
| I.2 | cyclopropyl | 0 | — | — | 4-Cl | CN | R | m.p. 87–90 |
| I.3 | cyclopropyl | 0 | — | — | 2,4-Cl₂ | CN | rac | m.p. 138–144 |
| I.4 | 2,2-dichloro-1-methylcyclopropyl | 0 | — | — | 4-Cl | CN | rac | |

TABLE B-continued
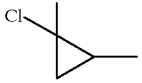
| No. | A | n | R³ | R⁴ | Z | Y | * | Phys. data (NMR in CDCl₃, data in ppm; m.p. in °C.) |
|---|---|---|---|---|---|---|---|---|
| I.5 |  | 0 | — | — | 4-Cl | CN | rac | |
| I.6 |  | 1 | CH₃ | H | 4-CH₃CN | CN | rac | $^1$H NMR: 0.2–0.9; 1.0; 1.2; 1.5; 2.3; 3.3; 3.5; 5.0; 6.4 (N-H); 7.2 |
| I.7 |  | 1 | CH₃ | H | 4-Cl | CN | rac | $^1$H NMR: 0.3–0.6; 1.0; 3.4; 8.7 |
| I.8 |  | 1 | CH₃ | H | 4-Cl | CN | R | $^1$H NMR: 0.2–0.9; 1.0; 1.2; 1.5; 3.3; 3.5; 5.0; 7.2 |
| I.9c [sic] |  | 1 | CH₃ | H | 2,4-Cl₂ | CN | rac | Oil |
| I.10 |  | 1 | CH₃ | CH₃ | 4-Cl | CN | R | $^{13}$C NMR: 20–25; 36; 48; 117; 128; 131; 142; 163 |
| I.11 | 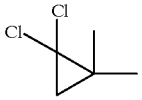 | 1 | CH₃ | CH₃ | 2,4-Cl₂ | CN | rac | m.p. 110–113 |
| I.12 | 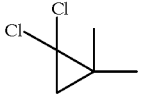 | 1 | CH₃ | H | 4-Cl | CN | R | $^1$H NMR: 1.0–1.5; 2.3; 3.3; 3.7; 5.0; 6.5; 7.2 |
| I.13 | 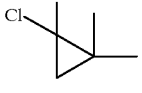 | 1 | CH₃ | H | 4-Cl | CN | rac | $^1$H NMR: 1.0–1.5; 2.3; 3.3; 3.7; 5.0; 6.5; 7.2 |
| I.14 | 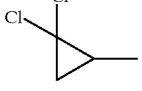 | 1 | CH₃ | H | 2,4-Cl₂ | CN | rac | $^1$H NMR: 1.0–1.5; 2.3; 3.3; 3.7; 5.0; 6.5; 7.2 |
| I.15 | 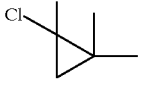 | 1 | CH₃ | CH₃ | 4-Cl | CN | rac | |
| I.16 |  | 1 | CH₃ | H | 4-CH₃ | CN | rac | MS: M⁺= 352 |

TABLE B-continued

| No. | A | n | R³ | R⁴ | Z | Y | * | Phys. data (NMR in CDCl₃, data in ppm; m.p. in ° C.) |
|---|---|---|---|---|---|---|---|---|
| I.17 | Cl, Cl-cyclopropyl-CH₃ | 1 | CH₃ | H | 4-OCH₃ | CN | rac | ¹H NMR: 1.2; 1.3; 1.5; 2.3; 6.3; 7.0 |
| I.18 | Cl, Cl-cyclopropyl-CH₃ | 1 | CH₃ | H | 4-Cl | CN | rac | MS: M⁺= 372 |
| I.19 | Cl, Cl-cyclopropyl-CH₃ | 1 | CH₃ | H | 4-Cl | CN | R | ¹H NMR: 1.2; 1.4; 1.5; 2.3; 3.7; 5.1; 6.5; 7.2 |
| I.20 | cyclopropyl | 1 | CH₃ | CH₃ | 4-Cl | CN | rac | MS: M⁺= 306 |
| I.21 | Cl, Cl-cyclopropyl-CH₃ | 1 | H | H | 4-Cl | CN | rac | MS: M⁺= 344 |
| I.22 | Cl, Cl-cyclopropyl-CH₃ | 1 | H | H | 4-Cl | CN | R | MS: M⁺= 344 |
| I.23 | cyclopropyl | 0 | — | — | 2,4-Cl₂ | CN | R | m.p. 140–145 |
| I.24 | cyclopropyl | 1 | CH₃ | CH₃ | 2,4-Cl₂ | CN | R | m.p. 75–80 |
| I.25 | cyclopentyl-dimethyl | 0 | — | — | 4-Cl | CN | rac | m.p. 95–100 |
| I.26 | cyclopentyl-dimethyl | 0 | — | — | 4-Cl | CN | R | m.p. 130–132 |
| I.27 | cyclopentyl-dimethyl | 0 | — | — | 2,4-Cl₂ | CN | rac | m.p. 110–115 |
| I.28 | cyclopentyl-dimethyl | 0 | — | — | 2,4-Cl₂ | CN | R | m.p. 120–123 |

TABLE B-continued

A―[R³/R⁴]ₙ―C(Y)―C(=O)―N―C²(CH₃)―C₆H₄―Z

| No. | A | n | R³ | R⁴ | Z | Y | * | Phys. data (NMR in CDCl₃, data in ppm; m.p. in °C.) |
|---|---|---|---|---|---|---|---|---|
| I.29 | cyclopropyl | 1 | $C_2H_5$ | H | 4-Cl | CN | R | ¹H NMR: 0.2–0.5; 0.7; 0.9–1.1; 1.4; 1.6; 3.5; 5.1; 6.5; 7.3 |
| I.30 | cyclopropyl | 1 | $C_2H_5$ | H | 2,4-$Cl_2$ | CN | R | ¹H NMR: 0.5; 0.7; 0.9–1.1; 1.4; 1.5; 3.5; 5.3; 6.7; 7.2; 7.4 |
| I.31 | cyclopropyl | 1 | $C_2H_5$ | $CH_3$ | 4-Cl | CN | R | ¹H NMR: 0.2–0.5; 0.7–1.0; 1.2; 1.5; 3.3; 5.1; 6.2; 7.3; |
| I.32 | cyclopropyl | 1 | $C_2H_5$ | $CH_3$ | 2,4-$Cl_2$ | CN | R | ¹H NMR: 0.3–0.5; 0.7–1.0; 1.4; 1.6; 3.4; 5.4; 6.5; 7.2; /.4 |

TABLE C (* = configuration at the atom labeled "*"; rac = racemic; R = R configuration)

V

A―[R³/R⁴]ₙ―C(Y)―C(=O)―N―C²(CH₃)―(2-naphthyl)

| No. | A | n | R³ | R⁴ | Y | * | Phys. data (NMR in CDCl₃, data in ppm; m.p. in °C.) |
|---|---|---|---|---|---|---|---|
| I.33 | 2,2-dichlorocyclopropyl | 0 | — | — | CN | rac | ¹H NMR: 0.8–1.3; 1.7; 3.6; 5.3; 6.5; 7.4; 7.8 |
| I.34 | cyclopropyl | 1 | $CH_3$ | H | CN | rac | m.p. 90–95 |
| I.35 | cyclopropyl | 1 | $CH_3$ | H | CN | R | m.p. 95–98 |
| I.36 | cyclopropyl | 1 | $CH_3$ | $CH_3$ | CN | rac | m.p. 145–148 |
| I.37 | cyclopropyl | 1 | $CH_3$ | $CH_3$ | CN | R | m.p. 105–108 |
| I.38 | cyclopropyl | 1 | $C_2H_5$ | H | CN | R | ¹H NMR: 0.4; 0.9–1.1; 1.4; 1.6; 3.5; 5.3; 6.6; 7.5; |

TABLE C-continued (* = configuration at the atom labeled "*"; rac = racemic;
R = R configuration)

V

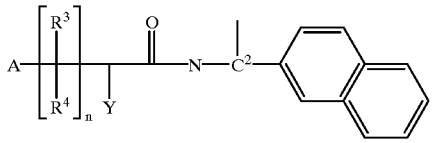

| No. | A | n | R³ | R⁴ | Y | * | Phys. data (NMR in CDCl₃, data in ppm; m.p. in ° C.) |
|---|---|---|---|---|---|---|---|
| I.39 | ▷ | 1 | C₂H₅ | CH₃ | CN | R | ¹H NMR: 0.4; 0.7–1.0; 1.4; 1.6; 3.4; 5.3; 6.4; 7.5; 7.8 |

Use Examples

The fungicidal action of the compounds of the formula I against harmful fungi was demonstrated by the following greenhouse experiments:

The active ingredients were formulated as a 20% emulsion in a mixture of 70% by weight of cyclohexanone, 20% by weight of Nekanil® LN (Lutensol® AP6, wetter with emulsifying and dispersant action based on ethoxylated alkylphenols) and 10% by weight of Emulphor® EL (Emulan® EL, emulsifier based on ethoxylated fatty alcohols) and diluted with water to give the desired concentration.

1. Activity Against *Pyricularia oryzae* (Protective)

Leaves of rice seedlings (cultivar "Tai-Nong 67") in pots were treated with the aqueous preparation of the active ingredients (comprising 250 ppm). After approximately 24 hours, the plants were inoculated with an aqueous spore suspension of *Pyricularia oryzae*. The plants which had been treated in this manner were placed for 6 days into controlled-environment cabinets at 22–24° C. and a relative atmospheric humidity of 95 to 99%. The extent of the disease which had developed on the leaves was subsequently determined visually.

In this test, the plants which had been treated with the compounds I.7, I.8 and I.10 according to the invention showed a disease level of 10% or less, while the disease level of the untreated plants was 80%.

2. Systemic Activity Against *Pyricularia oryzae*

Pregerminated rice (cultivar "Tai-Nong 67") was grown in a hydroponic system with Hoagland solution until it had reached the two-leaf stage. Then, the aqueous preparation of the active ingredient (comprising 50 ppm) was poured next to the roots. After the plants had grown on in the greenhouse for five days, they were inoculated with an aqueous spore suspension of *Pyricularia oryzae*. The plants which had been treated in this manner were placed for 6 days into controlled-environment cabinets at 22–24° C. and a relative atmospheric humidity of 95 to 99%. The extent of the disease which had developed on the leaves was subsequently determined visually.

In this test, the plants which had been treated with the compounds I.1, I.2, I.3, I.7, I.8 and I.10 according to the invention showed a disease level of 15% or less, while the disease level of the untreated plants was 80%.

3. Comparison against U.S. Pat. No. 4,946,867—Systemic Activity Against *Pyricularia oryzae*

The improved fungicidal activity of the compounds of the formula I according to the invention as compared to the structurally most similar compound of the prior art (U.S. Pat. No. 4,946,867) was demonstrated by the following experiment. The compound A (compound 9 from Table 1), known from U.S. Pat. No. 4,946,867, served as comparative compound

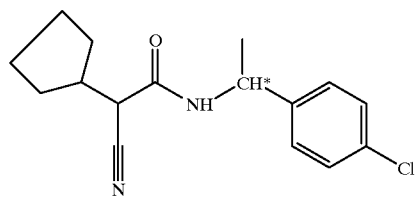

A

The experiment was carried out similarly to Use Example 2 using an aqueous active compound preparation containing 50 or 10 ppm.

| Active compound | % infestation of leaves after application of an aqueous active compound preparation containing . . . ppm | |
|---|---|---|
| | 50 | 10 |
| (according to the invention) I.1 | 5 | 20 |
| (comparative example) A | 40 | 65 |

Untreated (control) plants showed an infestation of 80%.

We claim:
1. A cycloalkylalkanecarboxamide of the formula I

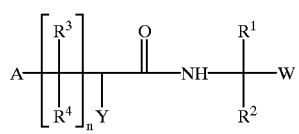

I where the substituents have the following meanings:
A is a substituted C₃–C₆-cycloalkyl;
R¹ is C₁–C₆-alkyl or C₂–C₆-alkenyl, it being possible for these radicals to be partially or fully halogenated and/or to have attached to them one or two of the following groups: $C_1$–$C_4$-alkoxy, $C_1$–$C_4$-haloalkoxy, $C_1$–$C_4$-alkylthio, $C_1$–$C_4$-alkoxycarbonyl, $C_3$–$C_6$-cycloalkyl and phenyl, it being possible for the phenyl to be partially or fully halogenated and/or have attached to it one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl or heterocyclyl;

$R^2$, $R^3$ and $R^4$ are hydrogen or, independently of this meaning, have one of the meanings of the radical $R^1$;

n is 0;

Y is cyano;

W is phenyl, naphthyl or heteroaryl which can have attached to it one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl and $C_1$–$C_4$-alkoxycarbonyl.

2. A cycloalkylalkanecarboxamide of the formula I as claimed in claim 1 where

A is $C_3$–$C_6$-cycloalkyl which has attached to it one to three substituents selected from the group consisting of halogen and $C_1$–$C_3$-alkyl.

3. A cycloalkylalkanecarboxamide of the formula I as claimed in claim 1 where

A is $C_3$–$C_6$-cycloalkyl which is methylated.

4. A cycloalkylalkanecarboxamide of the formula I as claimed in claim 1 where

A is $C_3$–$C_6$-cycloalkyl which carries the methyl substituent at the carbon linking the cycloalkane ring with the rest of the molecule.

5. A cycloalkylalkanecarboxamide of the formula I as claimed in claim 1 where

A is cyclopropyl which can have attached to it one to three substituents selected from the group consisting of halogen and $C_1$–$C_3$-alkyl.

6. A cycloalkylalkanecarboxamide of the formula I as claimed in claim 1, where A is cyclopropyl which is substituted by two chlorine atoms.

7. A cycloalkylalkanecarboxamide of the formula I as claimed in claim 1, where A is cyclopropyl which is substituted by an alkyl group on the carbon atom of the bonding site of the cyclopropane ring with the remainder of the molecule.

8. A cycloalkylalkanecarboxamide of the formula I as claimed in claim 1 where $R^1$ is methyl and $R^2$, $R^3$ and $R^4$ are hydrogen or methyl.

9. A cycloalkylalkanecarboxamide of the formula I as claimed in claim 1 where

W is phenyl, which can have attached to it one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl and $C_1$–$C_4$-alkoxycarbonyl.

10. A cycloalkylalkanecarboxamide of the formula I as claimed in claim 1 where

W is naphthyl, which can have attached to it one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-cycloalkyl and $C_1$–$C_4$-alkoxycarbonyl.

11. A process for the preparation of a cycloalkylalkanecarboxamide of the formula I as claimed in claim 1,

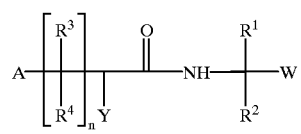

which comprises reacting a carboxylic acid derivative of the formula II

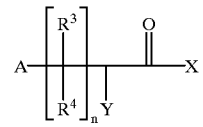

where the radicals A, Y, $R^3$ and $R^4$ and also n have the meanings given in claim 1, and X is a nucleophilically exchangeable radical with an amine of the formula III

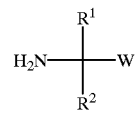

where the radicals W, $R^1$ and $R^2$ have the meanings given in claim 1.

12. A carboxylic acid derivative of the formula II

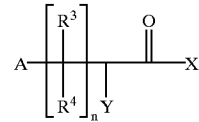

where

X is a nucleophilically exchangeable radical;

and A, n, $R^3$, $R^4$ and Y have the meanings given in claim 1.

13. A carboxylic acid derivative of the formula II as claimed in claim 12, where A is cyclopropyl which is substituted by two chlorine atoms.

14. A carbocyclic acid derivative of the formula II as claimed in claim 12 where A is cyclopropyl which has attached to it one to three substituents selected from the group consisting of chlorine and/or $C_1$–$C_3$-alkyl.

15. A carboxylic acid derivative of the formula II as claimed in claim 12, where A is cyclopropyl which is substituted by an alkyl group on the carbon atom of the bonding site of the cyclopropane ring with the remainder of the molecule.

16. A composition comprising such an amount of at least one cycloalkylalkanecarboxamide of the formula I as claimed in claim 1 that it is effective for controlling harmful fungi and at least one inert liquid and/or solid carrier and, if appropriate, at least one surfactant.

17. A method of controlling harmful fungi, which comprises treating the harmful fungi, their environment or the plants, areas, materials or spaces to be kept free from them with an effective amount of a cycloalkylalkanecarboxamide of the formula I as claimed in claim 1.

* * * * *